US012751790B2

(12) United States Patent
Themelis

(10) Patent No.: US 12,751,790 B2
(45) Date of Patent: Oct. 6, 2026

(54) SYSTEM, METHOD, AND COMPUTER PROGRAM FOR A SURGICAL MICROSCOPE SYSTEM AND CORRESPONDING SURGICAL MICROSCOPE SYSTEM

(71) Applicant: Leica Instruments (Singapore) Pte. Ltd., Singapore (SG)

(72) Inventor: George Themelis, Singapore (SG)

(73) Assignee: Leica Instruments (Singapore) Pte Ltd., Singapore (SG)

(*) Notice: Subject to any disclaimer, the term of this patent is extended or adjusted under 35 U.S.C. 154(b) by 870 days.

(21) Appl. No.: 18/068,592

(22) Filed: Dec. 20, 2022

(65) Prior Publication Data

US 2023/0190402 A1 Jun. 22, 2023

(30) Foreign Application Priority Data

Dec. 21, 2021 (DE) ..................... 10 2021 133 956.1

(51) Int. Cl.
*A61B 90/20* (2016.01)
*A61B 34/20* (2016.01)

(52) U.S. Cl.
CPC .............. *A61B 90/20* (2016.02); *A61B 34/20* (2016.02); *A61B 2034/2055* (2016.02)

(58) Field of Classification Search
CPC .... A61B 90/20; A61B 90/25; G02B 21/0012; G02B 21/00; G02B 21/0044; G02B 21/18; G02B 21/32; G02B 21/361; G02B 21/365; G06T 7/571
See application file for complete search history.

(56) References Cited

U.S. PATENT DOCUMENTS

| | | | | |
|---|---|---|---|---|
| 8,857,985 | B2 | 10/2014 | Zhou et al. | |
| 2001/0009473 | A1* | 7/2001 | Ogino | G02B 21/006 359/383 |
| 2013/0070249 | A1 | 3/2013 | Choi et al. | |
| 2016/0360961 | A1* | 12/2016 | Buckland | G02B 21/0012 |
| 2017/0199365 | A1* | 7/2017 | Czaniera | G02B 21/025 |
| 2019/0339502 | A1* | 11/2019 | Regensburger | G06T 7/593 |
| 2021/0157114 | A1* | 5/2021 | Pattison | G02B 27/58 |
| 2022/0079686 | A1* | 3/2022 | Piron | G06F 3/167 |
| 2022/0113524 | A1* | 4/2022 | Fischer | G02B 21/0032 |

FOREIGN PATENT DOCUMENTS

| | | | |
|---|---|---|---|
| CN | 106796340 | B | 10/2019 |
| DE | 102004006066 | B4 | 12/2005 |
| DE | 102018110641 | B3 | 7/2019 |
| DE | 102019118510 | A1 | 1/2021 |

* cited by examiner

*Primary Examiner* — Thomas K Pham
*Assistant Examiner* — Jennifer A Jones
(74) *Attorney, Agent, or Firm* — 2SPL Patent Attorneys PartG mbB; Kieran O'Leary

(57) ABSTRACT

Examples relate to a system, method, and computer program for a surgical microscope system, and to a corresponding surgical microscope system. The system is configured to determine a depth characteristic of a surgical site being imaged using a microscope. The system is configured to adjust a numerical aperture of the microscope based on the depth characteristic of at least a portion of the surgical site.

16 Claims, 4 Drawing Sheets

SYSTEM, METHOD, AND COMPUTER PROGRAM FOR A SURGICAL MICROSCOPE SYSTEM AND CORRESPONDING SURGICAL MICROSCOPE SYSTEM

CROSS-REFERENCE TO RELATED APPLICATION

This application claims priority to German Application 10 2021 133 956.1, which was filed on Dec. 21, 2021. The content of this earlier filed application is incorporated by reference herein in its entirety.

TECHNICAL FIELD

Examples relate to a system, method, and computer program for a surgical microscope system, and to a corresponding surgical microscope system.

BACKGROUND

Microscopes, such as microscopes used in surgical microscope system, are optical systems that comprise various optical components. One optical component of a microscope is the iris, which is an adjustable opening that controls how much light reaches the oculars or the optical imaging sensor(s) of the microscope. If the opening of the iris is bigger, more light passes through the iris and reaches the oculars or the optical imaging sensor(s). This generally increases the resolution of the view or image, but decreases the so-called depth of field, which is a distance interval, in which the view on the sample being viewed or captured appears sharp. If the opening of the iris is smaller, less light passes through. This increases the depth perception, but there is a decrease in resolution. In surgical microscopy, the opening of the iris is generally not adapted to the situation, i.e., the surgical procedure being performed, so the surgeon might not be provided with the optimal view. The position of the iris is typically at a fixed position, as manual adjustment would be an additional burden for the surgeon. Moreover, manual adjustment may lead to image quality degradation the iris opening is improperly adjusted or forgotten.

There may be a desire for an improved concept for operating a surgical microscope system.

SUMMARY

This desire is addressed by the subject-matter of the independent claims.

The proposed concept is based on the insight, that the image quality in a given surgical situation is often sufficiently good, but less then the maximum that the optics can provide if the iris settings were improved. To improve the image quality, a trade-off between image resolution and depth of field can be made in view of the surgical scenario at hand. In particular, the trade-off may be made in view of the depth characteristic of the surgical site, as the depth characteristic is a major factor in selecting the desired depth of field. Accordingly, the iris setting, i.e., the numerical aperture of the microscope, may be set to accommodate the depth characteristic of the surgical site, i.e., to obtain a depth of field that is suitable for the surgical scenario, resulting in an improvement of the image quality.

Various examples of the present disclosure relate to a system for a microscope of a surgical microscope system. The system comprises one or more processors and one or more storage devices. The system is configured to determine a depth characteristic of a surgical site being imaged using the microscope. The system is configured to adjust a numerical aperture of the microscope based on the depth characteristic of at least a portion of the surgical site. As outlined above, this may result in an improvement of the image quality.

In various examples, the system may be configured to determine a depth of field of at least the portion of the surgical site, and to adjust the numerical aperture of the microscope based on the depth of field. The depth of field, which may be the desired depth of field of the depth of field covering at least the portion of the surgical site, may be derived from the depth characteristic. The numerical aperture of the microscope influences the depth of field of the view on the surgical site and may thus be adjusted based on the determined depth of field. Consequently, the system may be configured to adjust the numerical aperture such that the depth of field provided by the microscope matches the depth of field of at least the portion of the surgical site.

Surgeons often use surgical microscopes day in, day out, for many hours at a time. Consequently, they develop personal preferences with respect to microscope settings. For example, some surgeons prefer a wider depth of field, so that even portions of the field of view that slope upwards or downwards appear sharp in the view, while some surgeons prefer the increased resolution of limiting the depth of field precisely on the region of interest of the surgical site. Accordingly, the system may be configured to adjust the numerical aperture such that the depth of field provided by the microscope is further suitable for a personal preference with respect to depth of field of a surgeon using the surgical microscope system.

As mentioned above, within the surgical site, a region may be of particular interest to the surgeon, i.e., as the surgeon currently operates in the region. The system may be configured to determine a region of interest within the surgical site. The system may be configured to adjust the numerical aperture of the microscope based on the depth characteristic of the region of interest within the surgical site. Accordingly, other portions of the surgical site (that also appear in the field of view of the microscope) may be disregarded when adjusting the numerical aperture of the microscope.

There are various ways for determining said region of interest. For example, the system may be configured to obtain imaging sensor data from an optical imaging sensor of the microscope. The system may be configured to determine the region of interest based on the imaging sensor data. In particular, the system may be configured to perform image processing on the imaging sensor data to determine a portion of the surgical site being operated on, and to determine the region of interest based on the portion of the surgical site being operated on. Alternatively, or additionally, object detection may be performed to identify a visual marker (such as a circle highlighting a portion of the surgical site), fluorescence emissions or tissue that is likely of interest to the surgeon. These visual clues may be used to define the region of interest without requiring additional involvement of the surgeon.

Alternatively, or additionally, the system may be configured to determine the region of interest based on a user input signal obtained via a user interface of the surgical microscope system. In other words, the region of interest may be manually defined by a surgeon (or an assistant), e.g., via a touch screen or a pointing device.

In some examples, additional measurement hardware may be used to determine the depth characteristic. For example, the system may be configured to obtain sensor data from a depth sensor of the surgical microscope system, and to determine the depth characteristic of at least the portion of the surgical site based on the sensor data of the depth sensor. For example, an (optical or ultrasound-based) Time-of-Flight sensor, a structured light sensor, or a separate pair of stereo photogrammetry sensors may be used for this purpose.

Image processing may also be used to determine the depth characteristic of the surgical site. For example, the system may be configured to obtain imaging sensor data from the optical imaging sensor of the microscope, and to determine the depth characteristic of at least the portion of the surgical site based on the imaging sensor data. For example, techniques such as structured light-based depth measurements, numerical aperture sweeping or focus sweeping may be used to determine the depth characteristic.

In some examples, different numerical aperture settings may be applied, and the resulting image quality may be compared in order to determine the depth characteristic. In other words, the numerical aperture sweeping may be performed. In this case, the system may be configured to sweep the numerical aperture of the microscope for the generation of a plurality of frames of imaging sensor data being based on different numerical apertures, and to determine the depth characteristic of at least the portion of the surgical site based on the plurality of frames of imaging sensor data being based on the different numerical apertures. Once the image quality does not significantly increase when the numerical aperture is decreased (i.e., when the diameter of the opening is decreased), the depth of field of the microscope may match the depth profile of at least the portion of the surgical site. To determine the image quality, the contrast and/or the presence of high spatial frequencies of the image frames may be analyzed—the more contrast and the more high spatial frequencies there are, the more areas of the surgical site may be considered to be sharp in the imaging sensor data. Accordingly, the system may be configured to determine the depth characteristic of at least the portion of the surgical site based on a contrast and/or based on a presence of spatial frequencies above a pre-defined spatial frequency threshold of the respective frames of the plurality of frames.

The sharpness of the image is not only dependent on the numerical aperture, but also based on whether the focal/working distance being used is appropriate. Accordingly, the focal/working distance may also be taken into account when determining the depth profile. The system may be configured to control the microscope or surgical microscope system to perform a sweep of a working distance and/or focal distance of the microscope for the generation of a further plurality of frames of imaging sensor data being based on different working distances or focal distances, and to determine the depth characteristic of at least the portion of the surgical site based on the further plurality of frames of imaging sensor data being based on the different working distances or focal distances. For example, the system may be configured to select a working distance or focal distance based on frames of the further plurality of frames of imaging sensor data generated during the sweep of the working distance or focal distance, and to sweep the numerical aperture of the microscope while using the selected working distance or focal distance for the generation of the plurality of frames of imaging sensor data being based on the different numerical apertures. In other words, a suitable focal/working distance may be set first to make sure that the depth of field is varied around a suitable starting point, and then the numerical aperture may be adjusted based on the selected focal/working distance Various examples of the present disclosure relate to a corresponding surgical microscope system comprising a microscope and the system as described above.

Various examples of the present disclosure relate to a corresponding method for a microscope of a surgical microscope system. The method comprises determining a depth characteristic of a surgical site being imaged using the microscope. The method comprises adjusting a numerical aperture of the microscope based on the depth characteristic of at least a portion of the surgical site.

Various examples of the present disclosure relate to a corresponding computer program with a program code for performing the above method when the computer program is executed on a processor.

BRIEF DESCRIPTION OF THE FIGURES

Some examples of apparatuses and/or methods will be described in the following by way of example only, and with reference to the accompanying figures, in which.

DETAILED DESCRIPTION

Various examples will now be described more fully with reference to the accompanying drawings in which some examples are illustrated. In the figures, the thicknesses of lines, layers and/or regions may be exaggerated for clarity.

Figure 1A:
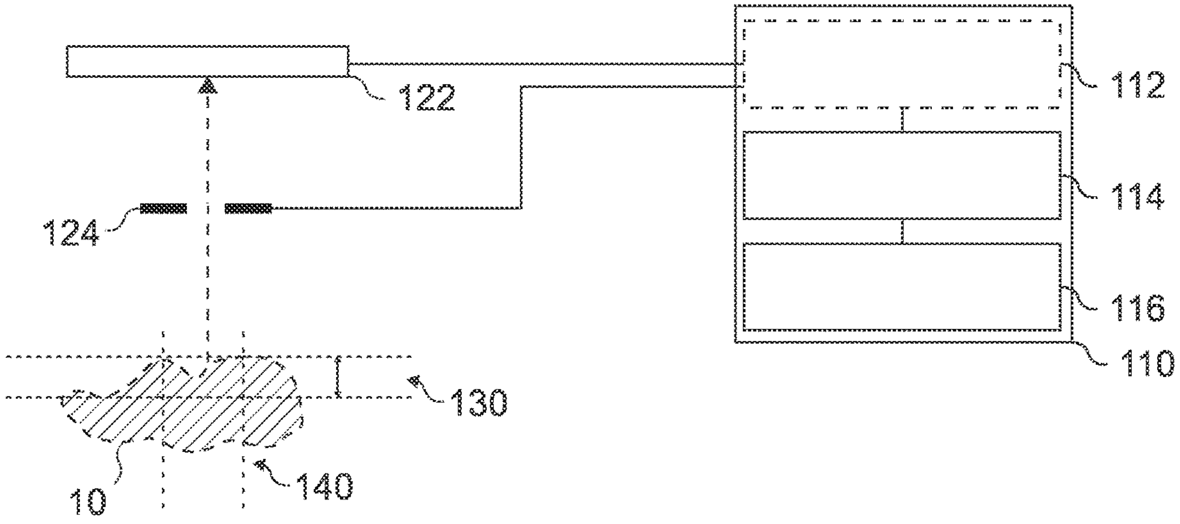
FIG. 1*a* shows a schematic diagram of an example of a system for a microscope of a surgical microscope system being coupled to various components of the microscope.

FIG. 1*a* shows a schematic diagram of an example of a system 110 for a microscope of a surgical microscope system being coupled to various components, such as an optical imaging sensor 122 and an iris 124, of the microscope. The system 110 is tasked with controlling various aspects of the microscope and of the entire surgical microscope system and/or with processing various types of sensor data of the surgical microscope system. Consequently, the system 110 may be implemented as a computer system, which interfaces with the various components of the surgical microscope system.

The system 110 comprises, as shown in FIG. 1*a*, one or more processors 114 and one or more storage devices 116. Optionally, the system further comprises one or more interfaces 112. The one or more processors 114 are coupled to the one or more storage devices 116 and to the optional one or more interfaces 112. In general, the functionality of the system is provided by the one or more processors, in conjunction with the one or more interfaces (for exchanging information, e.g., with the optical imaging sensor 122 of the microscope, with the iris 124 of the microscope, with a display device of the surgical microscope system, or with a depth sensor of the surgical microscope system) and/or with the one or more storage devices (for storing and/or retrieving information). The system is configured to determine a depth characteristic of a surgical site 10 being imaged using the microscope. The system is configured to adjust a numerical aperture of the microscope based on the depth characteristic of at least a portion of the surgical site. For example, the numerical aperture may be adjusted by controlling the iris 124 of the microscope.

FIG. 1*a* further highlights the resulting depth of field 130 and a region of interest 140 of the surgical site 10, which will be introduced in more detail at a later stage.

Figure 1B:
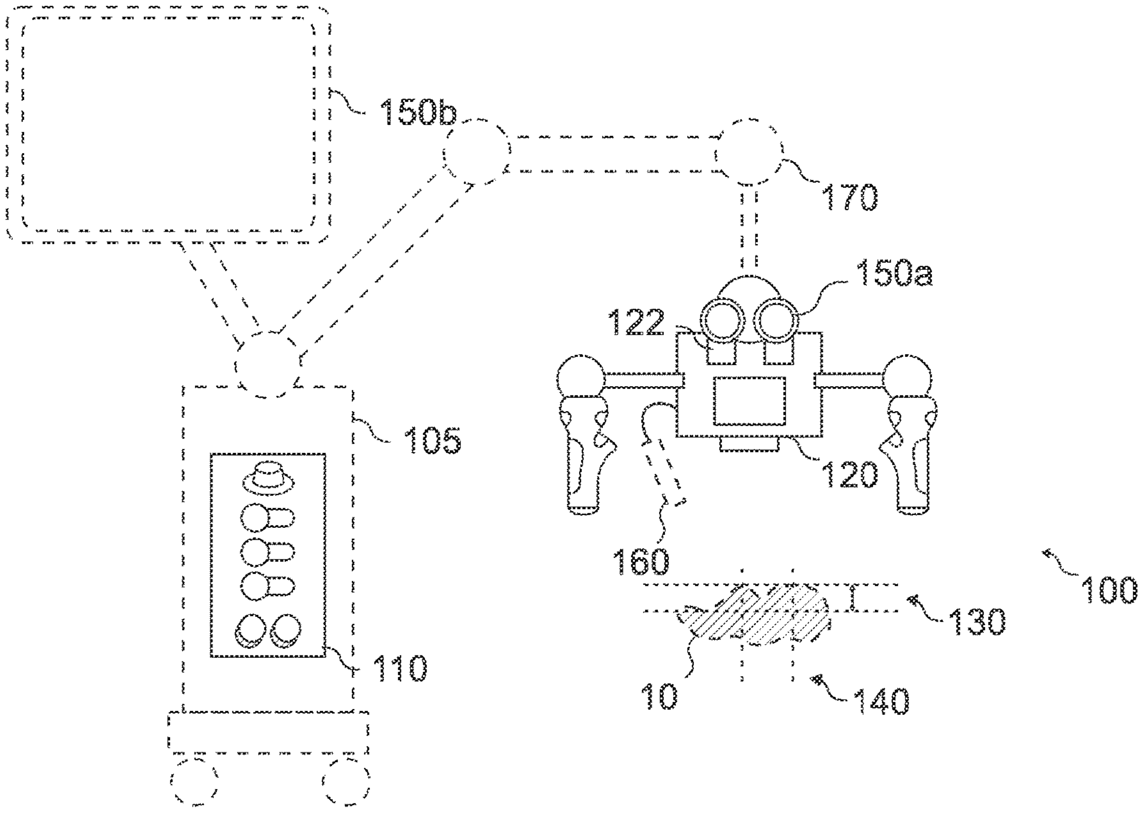
FIG. 1*b* shows a schematic diagram of an example of a surgical microscope system.

The optical imaging sensor 122 and the iris 124 are part of a microscope, for example of a microscope 120 of a surgical microscope system 100 as shown in FIG. 1*b*. In general, a microscope, such as the microscope 120, is an optical instrument that is suitable for examining objects that are too small to be examined by the human eye (alone). For example, a microscope may provide an optical magnification of a sample, such as a sample 10 shown in FIGS. 1*a*, 1*b*, 1*f* and 3. In modern microscopes, the optical magnification is often provided for a camera or an imaging sensor, such as the optical imaging sensor 122 of the microscope 120. The microscope 120 may further comprise one or more optical magnification components that are used to magnify a view on the sample, such as an objective (i.e., lens).

There are a variety of different types of microscopes. If the microscope is used in the medical or biological fields, the object 10 being viewed through the microscope may be a sample of organic tissue, e.g., arranged within a petri dish or present in a part of a body of a patient. In the present disclosure, the microscope 120 is a microscope of a surgical microscope system, i.e., a microscope that is to be used during a surgical procedure, such as an oncological surgical procedure or during tumor surgery. Accordingly, the object being viewed through the microscope, and shown in the image data, may be a sample of organic tissue of a patient, and may be in particular be the surgical site that the surgeon operates on during the surgical procedure.

FIG. 1*b* shows a schematic diagram of an example of a surgical microscope system 100 comprising the microscope 120 and the system 110. In general, a (surgical) microscope system is a system that comprises a microscope 120 and additional components, which are operated together with the microscope. In other words, a microscope system is a system that comprises the microscope and one or more additional components, such as the system 110 (which is a computer system being adapted to control and, for example, process imaging sensor data of the microscope), an illumination system (which is used to illuminate an object being imaged by the microscope), additional sensors, displays etc.

The surgical microscope system 100 shown in FIG. 1*b* comprises a number of optional components, such as a base unit 105 (comprising the system 110) with a (rolling) stand, ocular displays 150*a* that are arranged at the microscope 120, an auxiliary display 150*b* that is arranged at the base unit, a depth sensor 160, and a (robotic or manual) arm 170 which holds the microscope 120 in place, and which is coupled to the base unit 105 and to the microscope 120. In general, these optional and non-optional components may be coupled to the system 110, which may be configured to control and/or interact with the respective components.

The proposed concept is implemented primarily by the system 110, which determines the depth characteristic of the surgical site and adjusts the iris 124 of the microscope 120 according to the depth characteristic. In the following, the basic relationship between the numerical aperture and the depth characteristic is introduced.

The resolving power of a microscope in the focal plane of the objective of the microscope is limited by the diffraction of the light, which is, in turn, determined by the numerical aperture of the microscope. In particular, the maximum resolving power, and thus resolution, is proportional to the numerical aperture. In effect, a high resolution depends on a high numerical aperture, which is obtained by increasing the size of the opening of the iris.

However, the numerical aperture has a major impact on the depth of field of the microscope, i.e., the sharpness of the portions of the object being imaged that lie outside the focal plane. A large numerical aperture results in a shallow depth of field, such that variations of the distance between the object being imaged and the objective and sensor of the microscope lead to more portions of the object appearing out of focus.

Since both high resolution and increased depth of field are desirable properties in microscopy, a trade-off is established: The numerical aperture is adjusted based on the depth characteristic of the surgical site.

In the present context, the depth characteristic (or depth profile) of the surgical site may relate to, or be based on, the distance between points on the surface of the surgical site and the microscope. For example, the depth characteristic may comprise a three-dimensional representation (e.g., a three-dimensional model) of the surface of the surgical site (e.g., based on the distance between the surgical site and the microscope). In some examples, the depth characteristic may comprise information on a maximal and minimal distance between points located in at least the portion of the surgical site and the microscope.

In some examples, the actual distance may be of less importance, and not be included (directly) in the depth characteristic. In the present concept, the depth characteristic characterizes the depth profile of the surgical site. The relevant aspect of the depth profile is the effect it has on the sharpness of the view on the surgical site at a given numerical aperture and focal distance or working distance. Consequently, the depth characteristic may be defined with respect to a proportion of at least the portion of the surgical site that is deemed to be in focus (around the focal plane), i.e., that appears (sufficiently) sharp in the view.

The depth characteristic of the depth characteristic is also related to the depth of field of at least the portion of the surgical site, i.e., the depth of field required such that the entire portion (or at least a proportion thereof, e.g., at least 80%, at least 90% or at least 95%) of the surgical site appears sharp in the view. Accordingly, by determining the depth characteristic, the depth of field of at least the portion of the surgical site may be determined. The system may be configured to determine the depth of field 130 of at least the portion of the surgical site, and to adjust the numerical aperture of the microscope based on the depth of field. In this context, the depth of field of at least the portion of the surgical site may be delimited by the smallest and largest distance of points within at least the portion of the surgical site from (the objective) of the microscope. The system may be configured to adjust the numerical aperture such that the depth of field provided by the microscope matches the depth of field of at least the portion of the surgical site. For example, the system may be configured to set the focal plane of the microscope (e.g., by varying the working distance or by performing a focusing operation) to the center of the depth of field of at least the portion of the surgical site, and to select the numerical aperture of the microscope such, that the depth of field of the microscope matches the depth of field of at least the portion of the surgical site.

Since surgeons often spend hours at a time with a surgical microscope, with the surgical microscope being their main means of inspecting the surgical site, they develop preferences with respect to the optical properties of their view. For example, some surgeons may prefer resolution over depth of field, in effect keeping a shallow depth of field around the main surface of the surgical site, while tuning out less sharp portions of the surgical site that are not directly relevant to the surgical procedure being performed. Other surgeons prefer to see all (or nearly all) of the surgical site sharp, e.g., to be able to spot occurrences outside the small region they are operating on. Accordingly, the system may be configured to adjust the numerical aperture such that the depth of field provided by the microscope is further suitable for a personal preference with respect to depth of field of a surgeon using the surgical microscope system. For example, information on the preference of the surgeon, i.e., to prioritize resolution over depth of field or vice versa, may be stored in a storage device of the system, and the system may be configured to select the numerical aperture such, that the depth of field is suitable in view of the personal preference of the surgeon, e.g., by increasing the numerical aperture relative to a (neutral) numerical aperture being determined without reference to a personal preference of a surgeon if the personal preference of the surgeon indicates that the surgeon prioritizes a higher resolution over an increased depth of field, and by decreasing the numerical aperture relative to the neutral numerical aperture if the personal preference of the surgeon indicates that the surgeon prioritizes an increased depth of field over an increased resolution. For example, the system may be configured to determine the personal preference of the surgeon, e.g., by logging adjustments being made by the surgeon from the neutral numerical aperture. In some examples, a machine-learning model may be trained, based on the determined neutral numerical aperture (as training input sample) and the numerical aperture chosen by the surgeon (as desired output) using a supervised learning algorithm, to determine the numerical aperture preferred by the surgeon from the neutral numerical aperture. The system may be configured to use said machine-learning model to determine the numerical aperture that is suitable for the personal preference of the surgeon based on the neutral numerical aperture.

The proposed concept is based on determining the depth characteristic of a surgical site 10 being imaged using the microscope. In some examples, e.g., as shown in FIG. 1*b*, a dedicated depth sensor, such as Time of Flight sensor or structured light sensor, may be used to determine the depth characteristic of the surgical site, e.g., by determining the distance between points on the surface of the surgical site and the microscope. In other words, the system may be configured to obtain (depth) sensor data from a depth sensor 160 of the surgical microscope system, and to determine the depth characteristic of at least the portion of the surgical site based on the sensor data of the depth sensor. The system may be configured to determine the distance between points on the surface of the surgical site and the microscope based on the (depth) sensor data of the depth sensor 160.

Alternatively, the in-built optical imaging sensor(s) of the microscope may be used to determine the depth characteristic of the surgical site. Accordingly, the system may be configured to obtain imaging sensor data from an optical imaging sensor 122 of the microscope, and to determine the depth characteristic of at least the portion of the surgical site based on the imaging sensor data. In the following, two approaches for determining the depth profile based on the optical imaging sensor(s) of the microscope are introduced.

In a first approach, stereo photogrammetry may be used to determine a three-dimensional scan of the surgical site. In many cases, microscopes of surgical microscope systems are stereo microscopes, using a pair of optical imaging sensors (one for each ocular display) to image the surgical site. This pair of optical imaging sensor may be used to obtain two sets of the imaging sensor data, and to perform stereo photogrammetry on the two sets of imaging sensor data to determine the three-dimensional scan of the surgical site. The system may be configured to determine the depth characteristic of the surgical site from the three-dimensional scan of the surgical site.

In a second approach, a sequence of images may be captured at different numerical aperture settings (and different focal or working distances), and the sharpness of the images may be compared to determine the depth characteristic of the surgical site. In other words, the system may be configured to sweep the numerical aperture of the microscope for the generation of a plurality of frames of imaging sensor data being based on different numerical apertures, and to determine the depth characteristic of at least the portion of the surgical site based on the plurality of frames of imaging sensor data being based on the different numerical apertures. In other words, the system may be configured to set a sequence of different numerical apertures (thereby sweeping the numerical aperture), and to obtain a separate image frame of the surgical site for each of the different numerical aperture settings (i.e., the plurality of frames of imaging sensor data). The system may then be configured to determine the depth characteristic of at least the portion of the surgical site by comparing the sharpness of the different images frames of the plurality of frames of imaging sensor data.

The sharpness of the different image frames may be determined based on the contrast of the respective images and/or based on the proportion of high spatial frequencies in the respective images. For example, the system may be configured to determine the depth characteristic of at least the portion of the surgical site based on a contrast and/or based on a presence of spatial frequencies above a pre-defined spatial frequency threshold of the respective frames of the plurality of frames.

For example, the system may be configured to determine the contrast of the respective images, e.g., by determining the ratio of the standard deviation and the mean value of the pixels of the image, or by doing kernel-based comparisons between individual pixels and their neighbors (i.e., adjacent pixels). The more portions of the image are sharp, the higher the contrast of the image generally is.

Figure 1C:
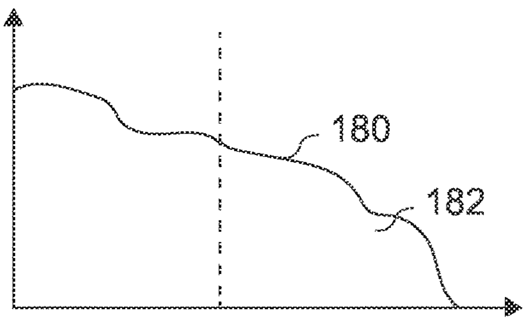
FIG. 1*c* shows a diagram of an example of a distribution of spatial frequencies in imaging sensor data.

The system may also be configured to determine the distribution of spatial frequencies of the respective images, e.g., by performing a 2D Fourier transform of the image. The higher the proportion of high spatial frequencies, the more fine-grained structures are visible in the image, which is the case if the respective portions of the image containing the fine-grained structures are perceived as sharp in the image. FIG. 1*c* shows a diagram of an example of a distribution of spatial frequencies in imaging sensor data. Graph 180 shows the distribution of spatial frequencies (with the x-axis denoting the spatial frequencies, and the y-axis denoting the amount of the respective spatial frequencies in the image), with portion 182 showing a portion of the distribution of the spatial frequencies above a pre-defined frequency threshold. By determining the integral of the portion of the distribution of the spatial frequencies above a pre-defined frequency, a quantitative measure can be determined that can be used to compare the presence of fine-grained structure in different images.

In general, even more important than an appropriate iris setting is that the surgical site is in focus, i.e., that the focal plane is at the surgical site. Since surgical sites tend to have a depth profile (in particular, when the surgeon operates in a wound tract or cavity), the process of adjusting the numerical aperture may comprise finding an appropriate starting point, i.e., an appropriate focal distance or working distance. Therefore, the system may be configured to control the microscope or surgical microscope system to perform a sweep of a working distance and/or focal distance of the microscope for the generation of a further plurality of frames of imaging sensor data being based on different working distances or focal distances, and to determine the depth characteristic of at least the portion of the surgical site based on the further plurality of frames of imaging sensor data being based on the different working distances or focal distances. In the present disclosure, the terms "working distance" and "focal distance" are used partially interchangeably, as, in surgical microscopy, the focal distance can be adjusted by changing the working distance, i.e., by moving the microscope closer or further away from the surgical site. However, both the working distance and the focal distance may be controlled independently.

Figure 1D:
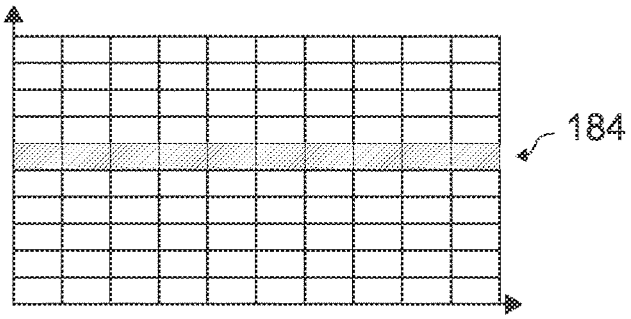
FIGS. 1*d* and 1*e* show diagrams of examples of a grid of combinations of working/focal distance and numerical aperture setting.
Figure 1E:
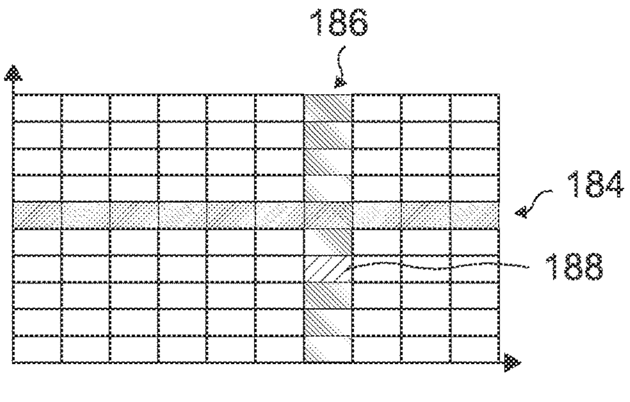

FIGS. 1*d* and 1*e* show diagrams of examples of a grid of combinations of working/focal distance and numerical aperture setting, highlighting the proposed approach according to an example. In FIGS. 1*d* and 1*e*, the x-axis denotes the working distance or focal distance, and the y-axis denotes the numerical aperture. A 10×10 grid is defined of combinations of 10 different numerical aperture settings and 10 different working distances/focal distances. However, other numbers of working/focal distances and aperture settings may be used as well. For example, as shown in FIG. 1*d*, the system may be configured to determine the further plurality of frames of imaging sensor data generated during the sweep of the working distance or focal distance based on a default numerical aperture setting (as indicated by cells 184 of the grid, which represent 10 further image frames taken at the same numerical aperture setting and different working/focal distances). As shown in FIG. 1*e*, the system may be configured to select a working distance or focal distance based on frames of the further plurality of frames of imaging sensor data generated during the sweep of the working distance or focal distance (e.g., by comparing the sharpness, i.e., the contrast and/or presence of spatial frequencies above the pre-defined spatial frequency threshold of the further plurality of image frames, and e.g., selecting the working/focal distance that yields the highest contrast or highest presence of spatial frequencies above the pre-defined spatial frequency threshold). The system may be configured to sweep the numerical aperture of the microscope while using the selected working distance or focal distance for the generation of the plurality of frames of imaging sensor data being based on the different numerical apertures (as indicated by cells 186 of the grid). The system may be configured to select a combination of working/focal distance and numerical aperture by comparing the plurality of image frames (again by comparing the sharpness, i.e., the contrast and/or presence of spatial frequencies above the pre-defined spatial frequency threshold of the plurality of image frames, and e.g., selecting the working/focal distance that yields the highest contrast or highest presence of spatial frequencies above the pre-defined spatial frequency threshold). In FIG. 1*e*, cell 188 is selected, which represents a combination of working/focal distance and numerical aperture.

In FIGS. 1*d* and 1*e*, an approach is shown that (eventually) performs an entire sweep across the whole range of numerical apertures and the whole range of working/focal distances. In other words, the system may be configured to perform the sweep of numerical apertures over an (entire) pre-defined range of numerical apertures supported by the microscope. Similarly, the system may be configured to perform the sweep of working or focal distances over an (entire) pre-defined range of working or focal distances supported by the microscope.

In some examples, another approach may be used, where the sweep starts from a starting point (e.g., the currently used numerical aperture and/or working/focal distance), and where the sweep is performed as long as the resulting sharpness of the image (as evidenced by the contrast or high spatial frequencies) improves (i.e., a heuristic approach). For example, the system may be configured to determine a starting working distance or focal distance, e.g., by using an autofocus functionality of the microscope, or by using the currently used working distance or focal distance. The system may be configured to sweep, starting from the starting working distance or focal distance, the working/focal distance as long as the sharpness of the resulting image frame improves (i.e., until a local maximum is identified with respect to sharpness of the image). Additionally, or alternatively, the system may be configured to determine a starting numerical aperture, e.g., the default numerical aperture, or by using the currently used numerical aperture. The system may be configured to sweep, starting from the starting numerical aperture, the numerical aperture as long as the sharpness of the resulting image frame improves (i.e., until a local maximum is identified with respect to sharpness of the image). For example, the sweep of the numerical aperture may be performed based on the working/focal distance identified in the sweep of the numerical/focal distance.

In some examples, multiple local maxima may be identified, e.g., by sweeping the working distance/focal distance or numerical aperture in two directions (i.e., lower and higher distance, smaller and larger numerical aperture) starting from the starting working/focal distance or starting numerical aperture. In other words, the respective sweep may be performed in two directions, e.g., by increasing and decreasing the working/focal distance or by increasing and decreasing the numerical aperture. For example, when the surgical site comprises a deep cavity with a projection at the bottom. In this case, the working/focal distance and/or iris settings may be used that yields the better overall image sharpness, or that yields the better overall image sharpness in the center of the image or in a region of interest.

In general, the numerical aperture may be adjusted continually. In other words, the system may be configured to repeat determining the depth characteristic and adjusting the numerical aperture, e.g., periodically, after the working distance of the microscope changes, or after the surgical site changes (as the surgeon has removed some tissue). In this case, it may be assumed that the currently used settings are at or near a local maximum. For example, when the depth characteristic is redetermined and the numerical aperture is readjusted, the currently used working/focal distance and/or numerical aperture may be used as starting working/focal distance and starting numerical aperture, respectively. For example, initially, full sweeps may be performed over the entire pre-defined range of working/focal distances and/or numerical apertures. When the numerical aperture is to be updated, the respective sweep or sweeps may be performed from the starting working/focal distance and starting numerical aperture, respectively.

While the field of view of surgical microscope is often very closely aligned with the surgical site (so the surgeon can see even finest details of the surgical site), in general, some amount of less-relevant periphery may still be visible in the field of view, e.g., so the surgeon can observe occurrences outside the immediate location the surgeon is operating on, such as bleeding. However, such occurrences might not need to be shown at maximal sharpness, as they are generally perceivable even if that portion of the image is slightly less sharp. Therefore, the proposed concept may be applied to only a portion of the field of view (i.e., a portion of the surgical site) that is of actual, or increased, interest to the surgeon. Consequently, the system may be configured to determine a region of interest 140 within the surgical site, and to adjust the numerical aperture of the microscope based on the depth characteristic of the region of interest within the surgical site. In other words, the proposed concept may be applied to the region of interest, giving less relevance to portions of the surgical site/field of view outside the region of interest.

In general, the region of interest may either be defined manually by the surgeon (or an assistant), or it may be derived from the optical imaging sensor. the system is configured to determine the region of interest based on a user input signal obtained via a user interface of the surgical microscope system. For example, the user interface may be a touch screen of the surgical microscope system. The surgeon or assistant may mark the region of interest via the touch screen, and the system may be configured to track the location of the region of interest across image frames.

Figure 1F:
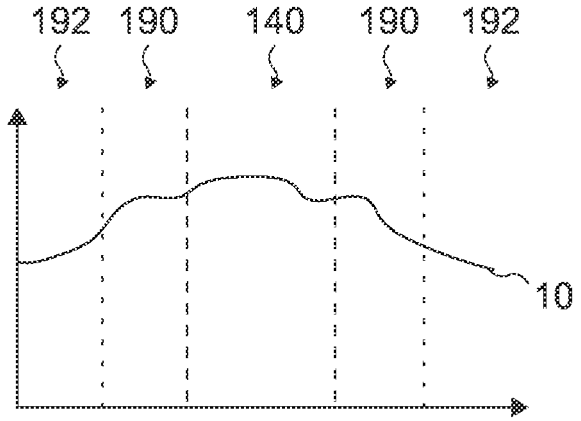
FIG. 1*f* shows a diagram of a depth profile of a surgical site.
Figure 1G:
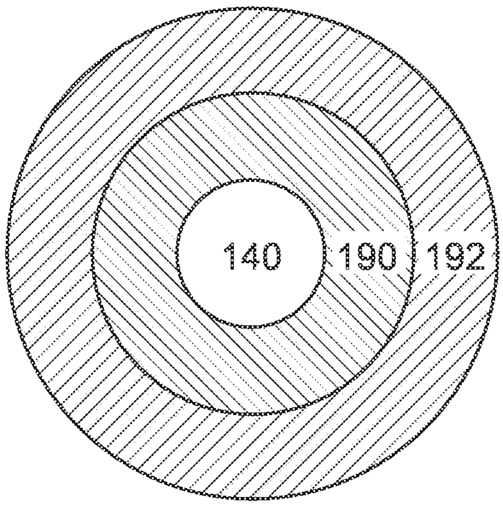
FIG. 1*g* shows a diagram of a top-down view on a surgical site.

Alternatively, the region of interest may be determined automatically. For example, as shown in FIGS. 1*f* and 1*g*, the center of the field of view may be considered to be the region of interest 140, followed by a region of medium interest 190 and a region of no interest 192. FIG. 1*f* shows a diagram of a depth profile of a surgical site 10 (with the x-axis showing the lateral dimension and the y-axis showing the vertical dimension of the depth profile). In the middle of the depth profile, the region of interest 140 is shown. Adjacent to the region of interest, a region 190 of medium interest is shown, followed by a region 192 of no interest. FIG. 1*g* shows a diagram of a top-down view on the same surgical site, with the region of interest 140 being surrounded by the region 190 of medium interest and the region of no interest 192. The system may be configured to use a weighting function to take into account the various regions, e.g., by giving a higher weight to the region of interest than to the region of medium interest or generally the rest of the field of view/surgical site in the comparison of the sharpness of the respective image frames.

Another approach is to analyze the content of the imaging sensor data. For example, the system may be configured to determine the region of interest based on the imaging sensor data of the optical imaging sensor of the microscope, e.g., by identifying the region of interest within the imaging sensor data. The system may be configured to perform image processing on the imaging sensor data to determine a portion of the surgical site being operated on, and to determine the region of interest based on the portion of the surgical site being operated on. For example, the system may be configured to determine the position of one or more surgical tools in the imaging sensor data, and to determine the portion of the surgical site being operated on based on the position of the surgical tools. For example, the system may be configured to use a trained machine-learning model to determine the portion of the surgical site being operated on, e.g., to determine the position of the one or more surgical tools within the imaging sensor data. For example, the trained machine-learning model may be trained based on annotated image data, e.g., with the image data being used as training samples and the location of the surgical site and/or the one or more surgical tools being used as desired output in a supervised learning-based training of the machine-learning model. Alternatively, the machine-learning model may be trained to detect one or more anatomical features, such as tumors, that are being operated on, e.g., using object detection. The system may be configured to determine the region of interest based on the detected one or more anatomical features.

Once the depth characteristic is determined, it is used to adjust the numerical aperture. This may be done by setting a numerical aperture that is appropriate in view of the depth characteristic. For example, a look-up table or function may be used to derive the numerical aperture for a given depth characteristic. If the depth characteristic is determined by sweeping working/focal distance and numerical apertures, the working/focal distance and numerical aperture setting that yielded the highest sharpness may be used. Alternatively, the lowest numerical aperture setting (i.e., the smallest opening) may be used that yields a (numerical) improvement over the next-higher numerical aperture setting (i.e., larger numerical aperture) that is greater than a (percentage) threshold. In other words, if the (numerical) improvement between a numerical aperture setting and the next-larger numerical aperture setting is smaller than the threshold, the improvement may be deemed too small (in view of the loss in resolution), and the next-larger numerical aperture may be used. In conclusion, the numerical aperture may be selected based on whether the improvement the numerical aperture makes on sharpness (relative to an adjacent numerical aperture, e.g., next larger numerical aperture) is greater than a pre-defined threshold.

In the proposed surgical microscope system, an optical imaging sensors is used to provide the optical imaging sensor. Accordingly, the optical imaging sensor is configured to generate the imaging sensor data. For example, the optical imaging sensor 122 of the microscope 120 may comprise or be APS (Active Pixel Sensor)—or a CCD (Charge-Coupled-Device)-based imaging sensor. For example, in APS-based imaging sensors, light is recorded at each pixel using a photodetector and an active amplifier of the pixel. APS-based imaging sensors are often based on CMOS (Complementary Metal-Oxide-Semiconductor) or S-CMOS (Scientific CMOS) technology. In CCD-based imaging sensors, incoming photons are converted into electron charges at a semiconductor-oxide interface, which are subsequently moved between capacitive bins in the imaging sensors by a circuitry of the imaging sensors to perform the imaging. The processing system 110 may be configured to obtain (i.e., receive or read out) the imaging sensor data from the optical imaging sensor. The imaging sensor data may be obtained by receiving the imaging sensor data from the optical imaging sensor (e.g., via the interface 112), by reading the imaging sensor data out from a memory of the optical imaging sensor (e.g., via the interface 112), or by reading the imaging sensor data from a storage device 116 of the system 110, e.g., after the imaging sensor data has been written to the storage device 116 by the optical imaging sensor or by another system or processor.

The one or more interfaces 112 of the system 110 may correspond to one or more inputs and/or outputs for receiving and/or transmitting information, which may be in digital (bit) values according to a specified code, within a module, between modules or between modules of different entities. For example, the one or more interfaces 112 may comprise interface circuitry configured to receive and/or transmit information. The one or more processors 114 of the system 110 may be implemented using one or more processing units, one or more processing devices, any means for processing, such as a processor, a computer or a programmable hardware component being operable with accordingly adapted software. In other words, the described function of the one or more processors 114 may as well be implemented in software, which is then executed on one or more programmable hardware components. Such hardware components may comprise a general-purpose processor, a Digital Signal Processor (DSP), a micro-controller, etc. The one or more storage devices 116 of the system 110 may comprise at least one element of the group of a computer readable storage medium, such as a magnetic or optical storage medium, e.g., a hard disk drive, a flash memory, Floppy-Disk, Random Access Memory (RAM), Programmable Read Only Memory (PROM), Erasable Programmable Read Only Memory (EPROM), an Electronically Erasable Programmable Read Only Memory (EEPROM), or a network storage.

More details and aspects of the system and surgical microscope system are mentioned in connection with the proposed concept, or one or more examples described above or below (e.g., FIGS. 2 to 4). The system and surgical microscope system may comprise one or more additional optional features corresponding to one or more aspects of the proposed concept, or one or more examples described above or below.

Figure 2:
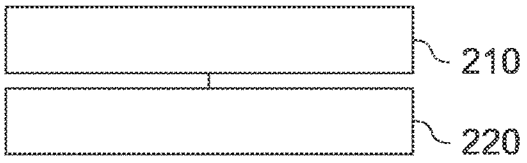
FIG. 2 shows a flow chart of an example of a method for a microscope of a surgical microscope system.

FIG. 2 shows a flow chart of an example of a method for a microscope of a surgical microscope system. The method comprises determining 210 a depth characteristic of a surgical site being imaged using the microscope. The method comprises adjusting 220 a numerical aperture of the microscope based on the depth characteristic of at least a portion of the surgical site.

For example, the method may be implemented by the system and/or the surgical microscope system introduced in connection with one of the FIGS. 1*a* to 1*g*. Features introduced in connection with the system or surgical microscope system of FIGS. 1*a* to 1*g* may likewise be included in the corresponding method.

More details and aspects of the method are mentioned in connection with the proposed concept, or one or more examples described above or below (e.g., FIG. 1*a* to 1*g*, 3 to 4). The method may comprise one or more additional optional features corresponding to one or more aspects of the proposed concept, or one or more examples described above or below.

Various examples of the present disclosure relate to a concept for automatic iris adjustment (or iris auto-adjustment).

The proposed concept is based on automatically adjusting the iris based on predefined criteria. These criteria may comprise the need for depth of field (or depth of focus). The need for depth of field or depth of focus may be estimated from the sharpness of the image. For example, the distance of different tissue areas from the camera may be measured. When the tissue is flat, there is no need for increased depth of field, and thus the iris could be opened to increase or optimize for resolution. For example, micro-adjustments of the focus and/or iris may be used to estimate what would be the optimal spot. As a result, a better in-depth perception may be achieved when entering cavities without the need for changing any settings. For example, when entering a cavity, the iris may be automatically closed, giving better in-depth perception to the surgeon.

Figure 3:
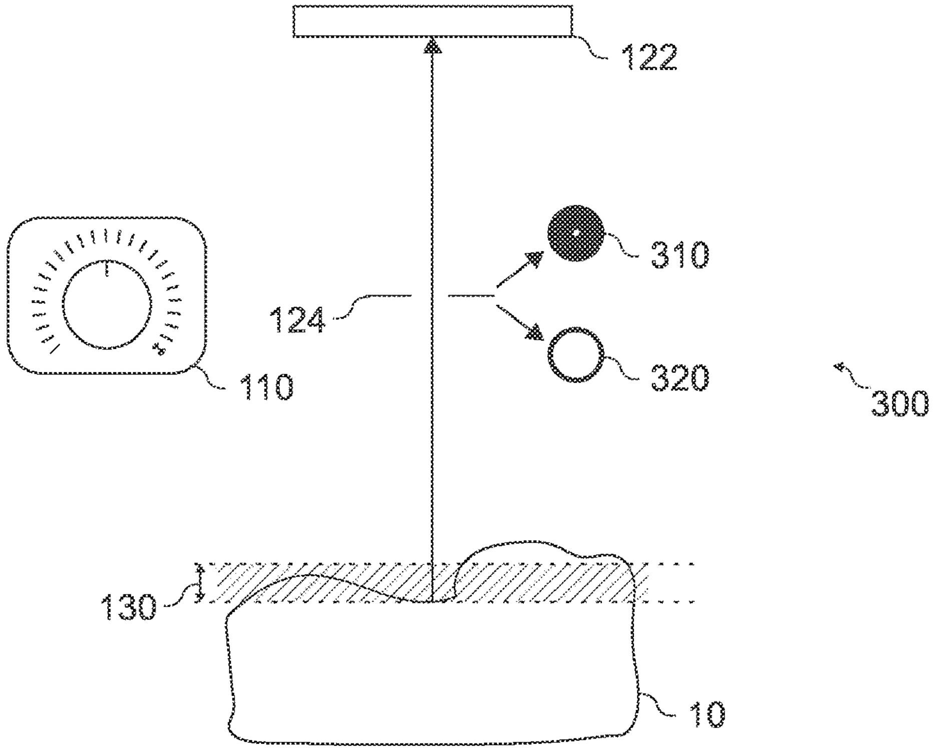
FIG. 3 shows a schematic diagram of an impact of an iris opening on a depth of field of the view of the microscope.
Figure 4:
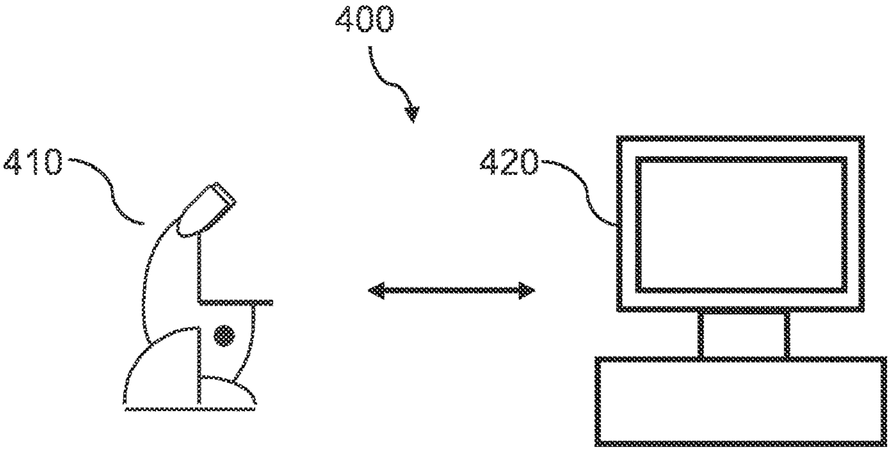
FIG. 4 shows a schematic diagram of an example of a system comprising a microscope and a computer system.

FIG. 3 shows a schematic diagram of an impact of an iris opening on a depth of field of the view of the microscope. FIG. 3 shows, similar to FIG. 1*a*, the optical imaging sensor 122 of the microscope, which is used to record the light arriving from the surgical site 10, with the light passing through the iris 124. An automatic iris adjustment system 110 (e.g., the system 110 introduced in connection with FIGS. 1*a* to 1*g*) is used to automatically adjust the iris 124, between a first setting 310 with a smaller opening, which reduces resolution while increasing the depth of field 130, and a second setting 320 with a large opening, which improves the resolution while decreasing the depth of field 130. The shown settings illustrate the extremes. Settings between these two settings may be used as well, establishing a trade-off between the resolution and the depth of field.

In some examples, the process may be applied only for a region of interest, which may be user-defined or automatically determined.

The estimation of the need for depth of field is directly related to the "unevenness" of the tissue, which may be represented by the depth characteristic of the surgical site. The unevenness or depth characteristic may be estimated by fast sequential capture of images with different iris settings, and comparing the sharpness of the image, or by performing a 3D scan of the surgical cavity, e.g., using various methods such as stereo photogrammetry.

In some examples, machine learning may be used for various purposes. For example, machine learning may be used to determine the region of interest, or to tailor the desired depth of field to the personal preferences of a specific surgeon.

More details and aspects of the proposed concept for automatic iris adjustment are mentioned in connection with the proposed concept or one or more examples described above or below (e.g., FIG. 1*a* to 2, 4). The proposed concept for automatic iris adjustment may comprise one or more additional optional features corresponding to one or more aspects of the proposed concept, or one or more examples described above or below.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some embodiments relate to a microscope comprising a system as described in connection with one or more of the FIGS. 1 to 3. Alternatively, a microscope may be part of or connected to a system as described in connection with one or more of the FIGS. 1 to 3. FIG. 4 shows a schematic illustration of a system 400 configured to perform a method described herein. The system 400 comprises a microscope 410 and a computer system 420. The microscope 410 is configured to take images and is connected to the computer system 420. The computer system 420 is configured to execute at least a part of a method described herein. The computer system 420 may be configured to execute a machine learning algorithm. The computer system 420 and microscope 410 may be separate entities but can also be integrated together in one common housing. The computer system 420 may be part of a central processing system of the microscope 410 and/or the computer system 420 may be part of a subcomponent of the microscope 410, such as a sensor, an actor, a camera or an illumination unit, etc. of the microscope 410.

The computer system 420 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 420 may comprise any circuit or combination of circuits. In one embodiment, the computer system 420 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 420 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 420 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 420 may also include a display device, one or more speakers, and a keyboard and/or controller, which can include a mouse, trackball, touch screen, voice-recognition device, or any other device that permits a system user to input information into and receive information from the computer system 420.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g. sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g. a classification algorithm, a regression algorithm or a similarity learning algorithm. Classification algorithms may be used when the outputs are restricted to a limited set of values (categorical variables), i.e. the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied and an unsupervised learning algorithm may be used to find structure in the input data (e.g. by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a pre-processing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge (e.g. based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g. of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data (e.g. in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

LIST OF REFERENCE SIGNS

The list of reference signs are:

10 Surgical site
100 Surgical microscope system
105 Base unit
110 System
112 One or more interfaces
114 One or more processors
116 One or more storage devices
120 Microscope
122 Optical imaging sensor
124 Iris
130 Depth of field
140 Region of interest
150*a* Ocular displays
150*b* Auxiliary display
160 Depth sensor
170 Arm
180 Spatial frequency distribution
182 Portion of spatial frequency distribution above threshold
184 Cells being used to sweep working distance/focal distance
186 Cells being used to sweep numerical aperture
188 Selected cell
190 Region of medium interest
192 Region of no interest
210 Determining a depth characteristic
220 Adjusting a numerical aperture
310 First setting with smaller opening
320 Second setting with larger opening
400 System
410 Microscope
420 Computer system

What is claimed is:

1. A system for a microscope of a surgical microscope system, the system comprising an optical imaging sensor, one or more processors, and one or more storage devices, wherein the system is configured to:

sweep a numerical aperture of the microscope for the generation of a plurality of frames of imaging sensor data from the optical imaging sensor, the frames being based on different numerical apertures;

determine a depth characteristic of at least a portion of a surgical site being imaged using the microscope based on the plurality of frames; and adjust the numerical aperture of the microscope based on the determined depth characteristic.

2. The system according to claim 1, wherein the system is configured to determine a depth of field of at least the portion of the surgical site, and to further adjust the numerical aperture of the microscope based on the depth of field.

3. The system according to claim 2, wherein the system is configured to adjust the numerical aperture such that the depth of field provided by the microscope matches the depth of field of at least the portion of the surgical site.

4. The system according to claim 3, wherein the system is configured to adjust the numerical aperture such that the depth of field provided by the microscope is further suitable for a personal preference with respect to depth of field of a surgeon using the surgical microscope system.

5. The system according to claim 1, wherein the portion of the surgical site is a region of interest, and wherein the system is configured to determine the region of interest within the surgical site.

6. The system according to claim 5, wherein the system is configured to determine the region of interest based on at least one of the imaging sensor data, a user input signal from a user interface of the system, or data from a gaze-tracking sensor.

7. The system according to claim 6, wherein when the region of interest is determined based on the imaging sensor data, the system is configured to perform image processing to determine the region of interest based on the portion of the surgical site being operated on.

8. The system according to claim 5, wherein the system is configured to determine the region of interest based on a user input signal obtained via a user interface of the surgical microscope system.

9. The system according to claim 1, wherein the system is configured to obtain sensor data from a depth sensor of the surgical microscope system, and to further determine the depth characteristic of at least the portion of the surgical site based on the sensor data of the depth sensor.

10. The system according to claim 1, wherein the system is configured to determine the depth characteristic of at least the portion of the surgical site based on a contrast and/or based on a presence of spatial frequencies above a predefined spatial frequency threshold of the respective frames of the plurality of frames.

11. The system according to claim 1, wherein the system is configured to control the microscope or surgical microscope system to perform a sweep of a working distance and/or focal distance of the microscope for the generation of a further plurality of frames of imaging sensor data being based on different working distances or focal distances, and to determine the depth characteristic of at least the portion of the surgical site based on the further plurality of frames of imaging sensor data being based on the different working distances or focal distances.

12. The system according to claim 11, wherein the system is configured to select a working distance or focal distance based on frames of the further plurality of frames of imaging sensor data generated during the sweep of the working distance or focal distance, and to sweep the numerical aperture of the microscope while using the selected working distance or focal distance for the generation of the plurality of frames of imaging sensor data being based on the different numerical apertures.

13. A surgical microscope system comprising a microscope and the system according to claim 1.

14. A method for a microscope of a surgical microscope system, the method comprising:

sweeping a numerical aperture of the microscope for the generation of a plurality of frames of imaging sensor data, the frames being based on different numerical apertures;

determining a depth characteristic of at least a portion of a surgical site being imaged using the microscope based on the plurality of frames; and adjusting the numerical aperture of the microscope based on the determined depth characteristic.

15. A non-transitory, computer-readable medium comprising a program code that, when the program code is executed on a processor, a computer, or a programmable hardware component, causes the processor, computer, or programmable hardware component to perform the method of claim 14.

16. A system for a microscope of a surgical microscope system, the system comprising one or more processors and one or more storage devices, wherein the system is configured to:

determine a depth characteristic of a surgical site being imaged using the microscope;

obtain imaging sensor data from an optical imaging sensor of the microscope;

determine a region of interest within the surgical site based on the imaging sensor data, wherein the system is configured to perform image processing on the imaging sensor data to determine a portion of the surgical site being operated on by determining a position of one or more surgical tools in the imaging sensor data, and to determine the region of interest based on the portion of the surgical site being operated on; and adjust a numerical aperture of the microscope for the region of interest within the surgical site based on the determined depth characteristic.

* * * * *